United States Patent [19]

Lundquist

[11] Patent Number: 5,233,096
[45] Date of Patent: Aug. 3, 1993

[54] ACIDIC CATALYST FOR CONDENSATION REACTIONS

[75] Inventor: Eric G. Lundquist, Yardley, Pa.

[73] Assignee: Rohm and Haas Company, Philadelphia, Pa.

[21] Appl. No.: 912,441

[22] Filed: Jul. 13, 1992

Related U.S. Application Data

[62] Division of Ser. No. 614,346, Nov. 16, 1990, abandoned.

[51] Int. Cl.$^5$ .................... C07C 37/20; C07C 39/12
[52] U.S. Cl. .................................................. 568/727
[58] Field of Search .................... 568/722, 727, 728; 521/33

[56] References Cited

U.S. PATENT DOCUMENTS

| | | | |
|---|---|---|---|
| 3,153,001 | 10/1964 | Apel et al. | 568/728 |
| 3,172,916 | 3/1965 | Wagner | 568/728 |
| 3,634,341 | 1/1972 | Gamill et al. | 568/728 |
| 3,922,255 | 11/1975 | Koestler et al. | 521/33 |
| 4,391,997 | 7/1983 | Mendiratta | 568/727 |
| 4,590,303 | 5/1986 | Mendiratta | 568/727 |
| 4,623,706 | 11/1986 | Timm et al. | 526/88 |
| 4,820,740 | 4/1989 | Li | 521/32 |

*Primary Examiner*—Werren B. Lone
*Attorney, Agent, or Firm*—John E. Taylor, III

[57] ABSTRACT

Strongly acidic cation-exchange resin beads made by functionalizing jetted, suspension-polymerized, crosslinked, styrenic copolymer beads with sulfonic acid groups produce an unexpectedly high level of conversion when catalyzing condensation reactions, particularly the condensation of phenol with aldehydes or ketones to form bisphenols.

7 Claims, No Drawings

ACIDIC CATALYST FOR CONDENSATION REACTIONS

This is a divisional of application Ser. No. 614,346, filed Nov. 16, 1990 abandoned.

This invention relates to acidic, polymeric catalysts for condensation reactions, and more particularly to strongly acidic, cation-exchange resin beads prepared from uniformly sized copolymer beads and useful as catalysts in acid-catalyzed reactions such as condensation reactions.

BACKGROUND OF THE INVENTION

Strongly acidic ion-exchange resins may replace mineral acids such as sulfuric acid and hydrochloric acid in catalyzing reactions, as for example condensation reactions. The use of the solid, acidic materials permits easier separation of the desired product from the catalyst in the reaction mixture, decreases equipment corrosion and complexity, and increased product purity. The use of the strongly acidic ion-exchange resins for catalyzing reactions is disclosed broadly in U.S. Pat. No. 3,037,052 to Bortnick, and the use of strongly acidic ion-exchange resins, prepared by sulfonating copolymers of styrene and polyethylenically unsaturated aromatic crosslinking monomers, as catalysts for the condensation of phenols with ketones or aldehydes to produce bisphenols, is disclosed in U.S. Pat. Nos. 3,153,001 to Apel et al., 3,172,916 to Wagner, 3,634,341 to Gammill et al., 4,590,303 and 4,391,997 to Mendiratta, 4,424,283 to Faler et al. and others. Of particular interest is their use to catalyze the condensation of phenol with acetone to produce Bisphenol-A (para, para'-isopropylidenediphenol), which is useful as a raw material for producing polycarbonates and epoxy resins.

The copolymer beads used to make ion-exchange resins are preferably spherical beads, and a uniform bead size throughout a particular batch of copolymer is desirable because it produces uniform, predictable hydraulic properties, such as flow rate and pressure drop, for a bed of the resin in a reaction vessel. Suspension polymerization, in which water-insoluble monomers are suspended and polymerized as discrete droplets in an aqueous medium, inherently produces beads that are generally spherical. The size of the beads depends upon the size of the monomer droplets that form, and various techniques are used to control the diameter and uniformity of the droplets. Additives are used in the aqueous phase to help control droplet size by varying the interfacial tension between the monomer and the aqueous medium; they also are used to limit the growth of coalescence of the monomer droplets. The intensity of agitation is also varied to help control the droplet size. Suspension polymerization has been used for over half a century to produce the copolymer intermediates for ion-exchange resins, as is disclosed for example by Boyer in U.S. Pat. No. 2,500,149, One technique that has been used to increase the uniformity of the droplet size is jetting a stream of monomer through an accurately sized orifice into the aqueous phase, as for example the process disclosed by Koestler et al. in U.S. Pat. No. 3,922,255.

SUMMARY OF THE INVENTION

I have discovered strongly acidic cation-exchange resin beads produced from crosslinked, styrenic copolymer beads which were formed by jetting the mixture of styrenic and crosslinker monomers into an aqueous liquid, and subsequently polymerizing the mixture, which beads produce surprisingly high reaction rates when used to catalyze condensation reactions. I have further discovered the process by which these resin beads are made, which comprises the steps of (a) jetting a mixture of one or more styrenic monomers, one or more crosslinking monomers and a free-radical polymerization initiator into a moving, aqueous suspending medium to form uniformly sized monomer droplets, (b) heating the droplets to a temperature above the activation temperature of the polymerization initiator until the droplets polymerize, (c) separating the resulting polymer beads from the suspending medium, (d) drying the beads, (e) functionalizing the beads with strongly acidic cation-exchange groups.

I have further discovered a process for catalyzing acid-catalyzed condensation reactions between reactions which comprises contacting the reactants with jetted, suspension-polymerized styrenic copolymer beads functionalized with strongly acidic cation-exchange groups. In the acid-catalyzed condensation of phenol with aldehydes or ketones, this process results in a surprisingly greater conversion of the aldehyde or ketone to the condensation product, compared with the conversion achieved with non-jetted, batch-polymerized cation-exchange resin beads.

DETAILED DISCUSSION OF THE INVENTION

The styrenic monomers useful in preparing the crosslinked copolymer beads of the present invention include styrene and substituted styrenes such as $\alpha$-methylstyrene, vinyltoluene, ethylvinylbenzene, vinylnaphthalene and the like. The crosslinking monomers containing a plurality of ethylenically unsaturated functional groups include aromatic crosslinking monomers such as divinylbenzene, divinyltoluene, trivinylbenzene, divinyl chlorobenzene, diallyl phthalate, divinylnaphthalene, divinyl xylene, divinylethylbenzene, trivinyl naphthalene and polyvinylanthracenes; and aliphatic crosslinking monomers such as di- and polyacrylates and methacrylates exemplified by trimethylolpropane trimethacrylate, ethylene glycol dimethacrylate, ethylene glycol diacrylate, neopentyl glycol dimethacrylate and pentaerythritol tetra- and trimethacrylates, and trivinylcyclohexane. The crosslinking monomer is preferably present at levels from about 0.1% to about 20 weight percent of the total monomer, and more preferably from about 1% to about 10 weight percent of the total monomer. Preferred crosslinking monomers are aromatic crosslinking monomers, and particularly preferred is divinylbenzene.

The jetting suspension-polymerization process useful for forming the crosslinked copolymer beads of the present invention is exemplified by, but not limited to, the process disclosed by Koestler et al. in U.S. Pat. No. 3,922,255, which is hereby incorporated into the present specification by reference. In that process a minimal solubility of the monomers in the aqueous suspending medium is important. Solubility can be decreased by adding an electrolyte to the aqueous suspending medium. The jetting process produces monomer droplets in the suspending medium whose average diameter for the droplet population is preferably varied over the range from about 20 $\mu$m to about 1 mm, and the resulting copolymer beads may be produced with an average diameter for the bead population which varies over the same range. The jetting suspension-polymerization process produces a droplet size distribution that is narrow, resulting in uniformly sized droplets and uniformly sized copolymer beads.

The monomers may be jetted by themselves, or mixed with inert liquids or prepolymers which are dissolved in the monomers or formed by prepolymerization of the monomers, or by a combination of both methods. The preferred jetting rate produces a ratio of suspending medium to monomer of from about 1.5:1 to about 10:1, and more preferably from about 2:1 to about 5:1. The monomer may be jetted into the suspending medium at a temperature about the activation temperature of the free-radical polymerization initiator described below, which will cause polymerization to begin almost immediately, or the medium may be below the activation temperature, but preferably above about 15° C., and be heated subsequently, after flowing into a heating zone; this will permit the monomer droplets to stabilize before polymerization begins.

All commonly used stabilizers, especially gelatin, starch, carboxymethylcellulose, polyacrylic acids, polyvinyl alcohol; or water-insoluble inorganic stabilizers in particulate form, such as bentonite, magnesium hydroxide and the like; or combinations of such stabilizers may be used to stabilize the monomer droplets in this or other jetting suspension-polymerization processes.

Free-radical polymerization initiators are preferred to initiate polymerization of the monomer droplets suspended in the suspending medium. Preferred free-radical polymerization initiators are oil-soluble initiators which are dissolved in the monomer, such as benzoyl peroxide, lauroyl peroxide, t-butyl peroctoate, t-butyl-peroxybenzoate, t-butylperoxypivalate, t-butylperoxy-2-ethylhexanoate, bis(4-t-butylcyclohexyl)peroxydicarbonate and the like; and azo compounds such as azobis-isobutyronitrile, azobisdimethylvaleronitrile and the like. The polymerization temperature, that is, the temperature at which the suspending medium is held during polymerization of the monomer droplets, and the polymerization initiator are interdependent in that the temperature must be high enough to break the chosen initiator down in to an adequate number of free radicals to initiate and sustain polymerization, that is, it must be above the activation temperature of the initiator. Preferred polymerization temperatures are from about 40° C. to about 100° C., and more preferably from about 50° C. to about 90° C., and the free-radical initiator is chosen so that it has an activation temperature below the polymerization temperature.

Other processes which form uniformly sized copolymer beads by jetting monomer into an aqueous suspending liquid may be used, as for example that disclosed by Timm et al. in U.S. Pat. No. 4,623,706, which uses a vibrating orifice to jet the monomer into the suspending medium. The suspending medium preferably moves with relation to the jetting orifice or orifices, and the monomer droplets may either by polymerized in the vicinity of the orifices by jetting the monomer into the suspending medium at the polymerization temperature, or they may be polymerized in a different zone of the polymerization apparatus by causing the moving suspending medium to carrying them into a heated polymerization zone. The polymerized beads may be separated from the suspension medium by gravity, by centrifugal flow, by hydraulic separation or by filtration.

Functionalization processes known to those skilled in the art may be used to functionalize the jetted copolymer beads with strong-acid functionality. The preferred strong-acid functionality is the sulfonic acid group, and known processes for sulfonating the copolymer may be used, including sulfonation processes which monosulfonate the aromatic ring and those which substitute the aromatic ring with more than a single sulfonic acid group. The preferred sulfonation produces a strongly acidic cation-exchange resin wit a cation-exchange capacity of from about 4.8 to about 5.4 milliequivalents per gram (dry basis) and a moisture-holding capacity of from about 60 to about 70%. Moisture-holding capacity, as used herein, refers to the amount of water a functionalized copolymer will retain, and is determined by weighing a drained but wet, functionalized copolymer sample, then drying the sample at mild conditions, e.g. 100°-110° C. and atmospheric pressure, to a constant weight, and reweighing the sample. Moisture-holding capacity is calculated as this weight difference, expressed as a percentage of the dried sample weight.

The reactions catalyzed by the strongly acidic cation-exchange resin beads of the present invention are those reactions that are catalyzed by the presence of strong acids, and include, but are not limited to, condensation reactions, for example the condensation of phenols with ketones or aldehydes to produce bisphenols. A preferred reaction which is catalyzed by the strongly acidic ion-exchange resin beads of the present invention is the reaction of phenol with acetone. More preferred is that reaction in which phenol and acetone are combined in a molar ratio of from about 20:1 to about 2:1 and the combination is contacted, at from about 40° C. to about 100° C., with from about 1 to about 40 weight percent (based on the weight of phenol and acetone) of the strongly acidic ion-exchange resin beads of the present invention, optionally in the presence of from about 1 to about 40 weight percent (based on the weight of phenol and acetone) of a mercaptan reaction promoter, preferably ethanethiol, aminoethane-thiol or dimethylthiazolidine.

As is shown by the following examples, use of the strongly acidic cation-exchange resin beads of the present invention in the condensation of phenols with aldehydes or ketones produces a higher conversion of the reactants to bisphenols than can be obtained with strongly acidic cation-exchange resin beads produced from batch-suspension-polymerized copolymer beads formed without jetting the monomer into the suspending medium, and this higher conversion is achieved without sacrificing the selectivity of the reaction for bisphenols. Without wishing to be bound by theory, I believe that the higher conversion results from a higher reaction rate achieved in the presence of the resin beads of the present invention. Given a long enough reaction time, the difference in conversion between jetted and non-jetted copolymer resin beads may disappear, but practical, commercial processes do not have unlimited time. The ability to produce more bisphenol product in a given time, which is afforded by a higher reaction rate in such processes, is an advantage that is readily apparent to those skilled in the art. The difference in reaction rate is all the more surprising because I am not aware of any theoretical basis for the difference between resin from jetted copolymer beads and that from beads formed without jetting.

The following examples are intended to illustrate the invention and not to limit it, except as it is limited in the claims. All ratios and percentages are by weight, unless otherwise indicated, and all reagents are of good commercial quality unless otherwise indicated. The catalysts used in the following examples are designated Catalyst K to indicate a comparative catalyst produced by suspension polymerization in a kettle, and Catalyst J to indicate a catalyst of the present invention produced by jetting suspension polymerization.

EXAMPLE 1

This example illustrates the preparation of the jetted copolymer beads useful in making the strongly acidic, cation exchange resin beads of the present invention.

An aqueous suspending medium was prepared containing 0.55% of Acrysol A-5 polyacrylic acid dispersant, 0.2% sodium hydroxide, 0.39% boric acid, 0.04% gelatin and 0.025% methylene blue, and having a pH of between 8.5 and 8.7. A monomer solution was prepared containing 7.3% commercial divinylbenzene (containing 55% pure divinylbenzene and 45% ethylvinylbenzene), 92.1% styrene 0.3% t-butyl peroctoate and 0.3% bis(4-t-butylcyclohexyl) peroxydicarbonate. The monomer mixture was jetted through vibrating jetting orifices 450 $\mu$m in diameter, at a rate of 145 kg/hr, into a stream of the suspending medium moving at a rate of 386 liter/hr. This dispersion was conveyed by the flow of suspending medium to a gelling column held at 63° C. The flow produced a residence time of 3.5 hours in the gelling column, and the conversion of monomer to copolymer during this time was 25%. As the suspension of copolymer exited the gelling column, additional 0.6% aqueous methylene blue solution was added at a rate of 2.8 liter/hour. The copolymer was separated from the aqueous phase, which was recycled. The copolymer was then held in a finishing kettle for 4 hours a 65° C., then transferred to a final finishing kettle and held at 80° C. for 1.5 hours, heated to 92° C., and held at that temperature for 1 hour. The finished copolymer was washed with water and air dried, for later sulfonation to Catalyst J.

EXAMPLE 2

This example illustrates the preparation of the comparative copolymer beads by a batch process which does not involve jetting the monomer into the suspending medium.

An aqueous suspending medium of 355 g water, 1.12 g gelatin, 0.83 g boric acid, and 13.78 g poly(diallyldimethylammonium chloride) dispersant was prepared and adjusted to a pH between 10.0 and 10.5. A monomer mixture was prepared containing 340.0 g styrene, 30.0 g commercial divinylbenzene (containing 55% pure divinylbenzene and 45% ethylvinylbenzene) and 1.42 g tert-butyl peroctoate. The monomer mixture was stirred into the suspending medium in a reaction vessel to form a suspension of monomer droplets. This suspension was blanketed with nitrogen, heated to 75° C., and held at that temperature for 5 hours, then heated to 98° C. and held at that temperature for 1 hour. The copolymer was then washed with water and air dried for later sulfonation to Catalyst K.

EXAMPLE 3

This example illustrates preparation of strongly acidic, cation-exchange resin beads from the copolymer beads of Examples 1 and 2.

In a glass lined vessel was mixed 190 g of copolymer from Example 1 or Example 2, 1450 g sulfuric acid (96.6%) and 65 g ethylene dichloride. This mixture was heated to 130° C., held at that temperature for 15 minutes and cooled to 120° C. The sulfonated resin was hydrated at a temperature between 95° C. and 110° C. by consecutive additions of water and removal of a volume of the resulting, diluted acid equal to the water added, until the removed liquid was essentially neutral. The acid free material was then removed from the vessel and drained. The properties of the two resulting catalysts are shown in Table I below.

TABLE I

| Catalyst | Cross-linker level | Cation Exchange Capacity | Moisture Holding Capacity | Bead Size |
|---|---|---|---|---|
| Catalyst K | 4% | 5.15 | 59.4% | 425–600 $\mu$m |
| Catalyst J | 4% | 5.10 | 60.2% | 4.25–600 $\mu$m |

This example illustrates the catalytic activity of the strongly acidic cation-exchange resins of the present invention in catalyzing the condensation of phenol and acetone to bisphenol-A.

To flasks containing 90 grams of 99+% phenol were added 10 (10% by weight) of dry catalyst K and catalyst J, respectively. The temperature was raised to, and held at, 75° C. and the phenol-catalyst mixture was stirred for one hour. Ten-milliliter portions of acetone (equivalent to a 7:1 phenol:acetone molar ratio) were added to each flash and the reaction was monitored as it proceeded at 75° C. by periodically removing 1-ml samples, quenching them with a water/methanol mixture and then analyzing them by high-pressure liquid chromatography. Acetone conversion is calculated as the area of the bisphenol-A peaks (both the ortho and para isomers), expressed as a percentage of the total area of the acetone peak and the bisphenol product peaks. Selectivity to bisphenol-A is calculated as the area of the bisphenol-A peaks (both the ortho and para isomers), expressed as a percentage of the total area of bispherol-A peaks and those of all other reaction products of phenol and acetone. These results are presented in Table II, below.

TABLE II

| Catalyst | Time | Acetone Conversion | Selectivity to BPA |
|---|---|---|---|
| Catalyst K | 1 hr | 54.6% | 85.3% |
| Catalyst J | 1 hr | 60.1% | 85.5% |

EXAMPLE 5

This example illustrates the effectiveness of the strongly acidic cation-exchange resins of the present invention in the presence of mercaptan reaction promoters.

To flasks containing 90 grams of 99+% phenol were added 10 grams (10% by weight) of dried catalysts K and J, respectively. Each catalyst used in this example had a particle size between 425 and 600 $\mu$m, and each had been treated with 7.5 millimoles of aminoethanethiol reaction promoter. The temperature was raised to, and held at, 75° C. and the flask contents were stirred for one hour. Ten-milliliter portions of acetone (equivalent to a 7:2 phenol:acetone molar ratio) were added to each flask, and the reaction was monitored as it proceeded at 75° C. by periodically removing 1-ml samples, quenching with a water/methanol mixture and then analyzing by high-pressure liquid chromatography. The resulting acetone conversion and selectivity to bisphenol-A, determined as described in Example 2, are presented in Table III, below.

TABLE III

| Catalyst | Time | Acetone Conversion | Selectivity to BPA |
| --- | --- | --- | --- |
| Catalyst KP | 1 hr | 80.2% | 97.3% |
| Catalyst JP | 1 hr | 88.4% | 96.9% |

I claim:

1. A process for catalyzing condensation reactions between phenols and aldehydes or ketones which yield bisphenols, which process comprises contacting the phenols and aldehydes or ketones with from about 1% to about 40% by weight, based on the total weight of the phenols and aldehydes or ketones, of jetted, suspension-polymerized styrenic copolymer beads functionalized with strongly acid cation-exchange groups.

2. The process of claim 1 wherein the reactants comprise phenol and an aldehyde or ketone.

3. The process of claim 2 wherein the reactants further comprise a mercaptan reaction promoter.

4. The process of claim 3 wherein the reaction promoter is present at from about 1 to about 40% by weight of the total reactants.

5. The process of claim 2 wherein the ketone is acetone.

6. The process of claim 5 wherein the phenol and acetone are present in a ratio of from about 20:1 to about 2:1.

7. The process of claim 1 wherein the temperature at which the reactants contact the beads is from about 40° C. to about 100° C.

* * * * *